(12) United States Patent
Sugimoto

(10) Patent No.: US 7,659,986 B2
(45) Date of Patent: Feb. 9, 2010

(54) SMOKE SENSOR AND ELECTRONIC EQUIPMENT

(75) Inventor: Kohichiroh Sugimoto, Nara (JP)

(73) Assignees: Sharp Kabushiki Kaisha, Osaka (JP); Fenwal Controls of Japan, Ltd., Tokyo (JP)

( * ) Notice: Subject to any disclaimer, the term of this patent is extended or adjusted under 35 U.S.C. 154(b) by 0 days.

(21) Appl. No.: 12/271,700

(22) Filed: Nov. 14, 2008

(65) Prior Publication Data

US 2009/0128821 A1    May 21, 2009

(30) Foreign Application Priority Data

Nov. 15, 2007    (JP)    ............................. 2007-296565

(51) Int. Cl.
G01N 21/00    (2006.01)

(52) U.S. Cl. .................. 356/438; 250/573; 340/628; 340/630

(58) Field of Classification Search ................. 356/437, 356/438; 250/573–574; 340/628, 630
See application file for complete search history.

(56) References Cited

U.S. PATENT DOCUMENTS 5,598,147 A * 1/1997 Mochizuki et al. .......... 340/630
6,876,305 B2 * 4/2005 Kadwell et al. ............. 340/630
7,483,139 B2 * 1/2009 Powell ....................... 356/438
2001/0020899 A1 * 9/2001 Kadwell et al. ............. 340/630

FOREIGN PATENT DOCUMENTS

| JP | 58-39552 U | 3/1983 |
| JP | 59-5398 A | 1/1984 |
| JP | 60-33035 A | 2/1985 |

* cited by examiner

Primary Examiner—Hoa Q Pham
(74) Attorney, Agent, or Firm—Birch, Stewart, Kolasch & Birch LLP

(57) ABSTRACT

In a smoke sensor, a first light-receiving element which receives light from a light-emitting element and is disposed in a position where the quantity of received light changes according to a density of smoke and a second light-receiving element which monitors the quantity of light of the light-emitting element are arranged symmetrically with respect to the light-emitting element. Furthermore, a signal from the first light-receiving element and a signal from the second light-receiving element are amplified by an identical amplifier circuit. In a microcomputer, the density of smoke is computed based on a difference between an output obtained by amplifying an output of the first light-receiving element with the amplifier circuit and an output obtained by amplifying an output of the second light-receiving element with the amplifier circuit.

8 Claims, 5 Drawing Sheets

SMOKE SENSOR AND ELECTRONIC EQUIPMENT

This nonprovisional application claims priority under 35 U.S.C. §119(a) on Patent Application No(s). 2007-296565 filed in Japan on Nov. 15, 2007, the entire contents of which are hereby incorporated by reference.

BACKGROUND OF THE INVENTION

1. Field of the Invention

The present invention relates to a smoke sensor and in particular to a smoke sensor which detects the density of smoke by emitting light and then receiving light reflected by the smoke or light which has passed through the smoke.

Furthermore, the present invention relates to electronic equipment having a smoke sensor and in particular to electronic equipment having a smoke sensor which detects the density of smoke by emitting light and then receiving light reflected by the smoke or light which has passed through the smoke.

The present invention also relates to a smoke sensor which is preferably mounted on an air cleaner, a fire alarm, a sprinkler, or the like.

2. Background Art

Conventionally, in a smoke sensor which detects the density of smoke by receiving light which has been emitted from a light source and then reflected by the smoke, because the quantity of the reflected light is very small, the output of a light-receiving element receiving the reflected light is very small. Therefore, the output of the light-receiving element is amplified by an amplifier circuit and it is determined that the smoke has been detected when the output of the amplifier circuit has reached a predetermined range.

However, the output changes affected by a change in the quantity of light emitted by an LED caused by a temperature change or deterioration or the like of the LED even if the density of smoke to be detected is in the same range. For this reason, there is a problem that smoke is detected outside a smoke density detection range which has been set. In order to overcome this problem, various correction methods have been proposed.

For example, it has been proposed that a thermistor is added to a light-emitting element driving circuit to make a temperature correction in order to correct a condition that the quantity of light emitted by a light-emitting element is reduced due to its temperature characteristic and the quantity of light reflected by smoke is thus reduced. In this connection, it has also been proposed that when an output changes due to the temperature characteristic of an IC, a thermistor is added to a resistor section deciding an amplification factor, and the amplification factor is changed by the thermistor to make a temperature correction when there is a temperature change.

Furthermore, it has also been proposed that a detector including a light-receiving element monitoring a reduction in the quantity of light emitted by an LED caused by its deterioration or the like is provided in addition to a detector including a light-receiving element detecting smoke and a change in an output signal of the light-receiving element monitoring the quantity of emitted light is fed back to a light-emitting element driving circuit to correct the quantity of emitted light.

Furthermore, it has also been proposed that in order to make a temperature correction, a light-receiving element detecting no smoke is provided in addition to a light-receiving element detecting smoke and the difference between the outputs of the two light-receiving elements is amplified to detect the difference between the outputs of the two light-receiving elements and thereby an output change caused by a temperature change is corrected.

The above conventional technologies have a problem that errors for which no cause is identified cannot be corrected, although an error for which a cause such as a temperature change or a change in the quantity of light of an LED caused by its deterioration is identified can be corrected.

For example, the technology which adds a thermistor to make a temperature correction is able to correct a temperature change but is not able to correct a change in the quantity of light emitted by an LED caused by its deterioration. This technology requires selection of a thermistor suitable for temperature correction and may not obtain a sufficient correction.

Furthermore, of the technologies which correct a reduction in the quantity of light emitted by an LED, the technology which uses a detector including a light-receiving element monitoring a reduction in the quantity of light emitted by the LED caused by its deterioration in addition to a detector including a light-receiving element detecting smoke, and feeds back a change in an output signal of the light-receiving element monitoring the quantity of emitted light to a light-emitting element driving circuit to correct the quantity of emitted light, is of course not able to correct for a temperature change, and what is worse is that the technology needs a significantly complicated configuration and an increased number of parts including the two detectors, etc.

Regarding the method, which provides a light-receiving element detecting no smoke in addition to a light-receiving element detecting smoke in order to make a temperature correction, amplifies the difference between outputs of the two light-receiving elements to detect a differential current between the two light-receiving elements, and thereby corrects an output change caused by a temperature change, this method has been conceived in a light extinction system in which the light-emitting element and the light-receiving elements are arranged facing each other.

In the light extinction type, the light-receiving element detecting no smoke also directly receives light, so that the two light-receiving elements have similar outputs under a condition of the same quantity of light of an LED and the same amplification factor at a normal time when there is no smoke, while when smoke has flowed into the smoke sensor, the differential current of the two light-receiving elements and hence the output of the amplifier increase and thereby the smoke can be detected. However, the light extinction type has a problem that the light-receiving element detecting smoke directly receives light from the light-emitting element when there is no smoke and the light-receiving element detecting no smoke always directly receives light from the light-emitting element, and therefore the light-receiving elements easily deteriorate.

On the other hand, in a reflection type, when there is no smoke, there is no light reflected by smoke and therefore a light-receiving element detecting smoke receives a small quantity of light and the output of it is small, while a light-receiving element detecting no smoke directly receives light and therefore the quantity of light received by it is large and the output of it is large. Thus, when the same quantity of light emitted by an LED and the same amplification factor are applied for each of the light-receiving elements, the output of the light-receiving element detecting no smoke becomes too large to be saturated and therefore a true difference may not be obtained.

The output difference obtained when there is no smoke is large. But, as the density of smoke increases, the output difference becomes smaller, and when the density reaches some value, the output difference becomes zero. If the density of smoke then further increases, the output difference increases again. Thus, depending on adjustment, the output difference obtained when there is no smoke may be the same as an output difference obtained when there is much smoke and therefore a correct detection may not be able to be done.

Furthermore, when the quantity of light emitted by an LED, an amplification factor, etc. are adjusted according to a light-receiving element detecting no smoke, an original smoke detection accuracy is reduced and therefore the density of smoke cannot be detected accurately.

SUMMARY OF THE INVENTION

Therefore, the present invention aims at providing a smoke sensor capable of correcting an error for which no cause is identified. The present invention also aims at providing electronic equipment having a smoke sensor capable of correcting an error for which no cause is identified.

A smoke sensor according to an aspect of the present invention comprises:

a light-emitting device emitting light;

a first chamber;

a smoke passage providing communication between inside of the first chamber and outside of the first chamber;

a second chamber having a density of smoke of a predetermined value;

a first light-receiving element receiving light which has traveled in the first chamber after being emitted from the light-emitting device directly to the first chamber or light which has traveled in the first chamber after being emitted from the light-emitting device and entering the first chamber through only a place having a density of smoke of zero;

a second light-receiving element receiving light which has traveled in the second chamber after being emitted from the light-emitting device directly to the second chamber or light which has traveled in the second chamber after being emitted from the light-emitting device and entering the second chamber through only a place having a density of smoke of zero;

a first switch receiving and selectively outputting a signal from the first light-receiving element and a signal from the second light-receiving element;

an amplifier section amplifying a signal from the first switch; and a density detecting section detecting a density of smoke in the first chamber on the basis of a first amplified signal which is a signal from the first light-receiving element amplified by the amplifier section and a second amplified signal which is a signal from the second light-receiving element amplified by the amplifier section.

In this specification, a chamber is defined as a region surrounded by an inner periphery which is not opened to the outside, or a region surrounded by an inner periphery which is opened to the outside at one place or two or more places. For this reason, in this specification, for example, a region surrounded by the inner periphery of a pan or a pot also constitutes a chamber. This example is an example having one opening. In this example, the region surrounded by the inner periphery of the pan refers to a region to be occupied by water when the pan put on a horizontal plane is fully filled with water.

According to this invention, an output of the first light-receiving element detecting smoke and an output of the second light-receiving element which is not influenced by smoke are caused by light emitted from the same light-emitting device, so that a change in the quantity of light emitted by the light-emitting device (e.g. a light-emitting element such as a light-emitting diode) caused by its temperature characteristic would result in similar changes in the outputs of the first and second light-receiving elements. Thus, when the quantity of light emitted by the light-emitting device is reduced due to its temperature characteristic, deterioration, or the like, the outputs of the first and second light-receiving elements change in similar proportions, so that the difference between an output from the first light-receiving element amplified by the amplifier section and an output from the second light-receiving element amplified by the amplifier section would change little. Thus, an output change caused by the temperature characteristic and deterioration of the light-emitting device is easily corrected.

Furthermore, according to this invention, an output from the first light-receiving element and an output from the second light-receiving element are amplified by the same amplifier section, so that the temperature characteristic of the amplifier section similarly influence the output from the first light-receiving element and the output from the second light-receiving element. Thus, a change in the difference between the output from the first light-receiving element amplified by the amplifier section and the output from the second light-receiving element amplified by the amplifier section is small and therefore an output change caused by the temperature characteristic of the amplifier section can be easily corrected. In short, because the output of the first light-receiving element detecting smoke and the output of the second light-receiving element which is not influenced by smoke are inputted to the same amplifier section, an output voltage is prevented from vary due to the amplifier circuit.

In one embodiment, each of the first amplified signal and the second amplified signal is a voltage signal. A light-receiving surface of the first light-receiving element is disposed in the first chamber and a light-receiving surface of the second light-receiving element is disposed in the second chamber, and a distance from a light-emitting surface of the light-emitting device to the light-receiving surface of the first light-receiving element is same as a distance from the light-emitting surface to the light-receiving surface of the second light-receiving element. The predetermined value of the density of smoke in the second chamber is zero, and a magnitude of the first amplified signal is same as a magnitude of the second amplified signal in a state that the density of smoke in the first chamber is zero.

According to this embodiment, the first light-receiving element and the second light-receiving element are arranged in positions symmetrical with respect to the light-emitting device, so that an output voltage of the first light-receiving element and an output voltage of the second light-receiving element in the case that there is no smoke can be made the same. The phrase "a magnitude of the first amplified signal is same as a magnitude of the second amplified signal" or similar phrases are intended to be interpreted as covering not only a case in which there is a difference of zero (i.e., no difference) between the output voltages of the first and second light-receiving elements but also a case in which there is an error margin in the difference. The error margin depends on a power supply voltage applied to the smoke sensor and reference voltages of the first and second amplified signals, and is for example 0.4 V-2.0 V when the power supply voltage applied to the smoke sensor is 3.0 V and the reference voltages of the first and second amplified signals are 0.3 V. Also, the phrase "a distance from a light-emitting surface of the light-emitting device to the light-receiving surface of the first light-receiving element is same as a distance from the light-emitting surface to the light-receiving surface of the second light-receiving element" and similar phrases are intended to be interpreted as covering a range of sameness that allows the difference between the magnitudes of the first and second amplitudes falls within a range of the above error margin when the density of smoke of the second chamber is zero.

In one embodiment, the amplifier section has one or more amplifiers.

In one embodiment, the amplifier section has a current-voltage conversion section. This current-voltage conversion section has an input terminal connected with an output terminal of the first switch, an output terminal, and a resistor device connected between the input terminal and the output terminal of the current-voltage conversion section. And, the resistor device provides resistances which are different between a case that a signal from the first light-receiving element is processed by the current-voltage conversion section and a case that a signal from the second light-receiving element is processed by the current-voltage conversion section.

In one embodiment, the resistor device includes a first resistor one end of which is connected with the input terminal of the current-voltage conversion section, and a second resistor one end of which is connected with the input terminal of the current-voltage conversion section. The current-voltage conversion section further has a second switch an output terminal of which is connected with the output terminal of the current-voltage conversion section. Also, the smoke sensor further comprises a control circuit which outputs a control signal for connecting an input terminal of the second switch to another end of the first resistor when a signal from the first light-receiving element is processed by the current-voltage conversion section, while outputting a control signal for connecting the input terminal of the second switch to another end of the second resistor when a signal from the second light-receiving element is processed by the current-voltage conversion section.

According to this embodiment, a gain of the current-voltage conversion section (e.g. an I-V conversion amplifier) can be changed and a gain resistor of the current-voltage conversion section (e.g. an I-V conversion amplifier) can be adjusted by trimming.

Thus, when an output voltage based on an output of the first light-receiving element and an output voltage based on an output of the second light-receiving element in the case that there is no smoke are not identical due to assay variations, molding variations in casing, or the like of the light-emitting device or the light-receiving elements, the smoke sensor can be adjusted by trimming the gain resistor in a state before installation such that the output voltage based on an output of the first light-receiving element and the output voltage based on an output of the second light-receiving element in the case that there is no smoke become substantially identical.

Furthermore, according to this embodiment, when individual variations of the two light-receiving elements are generated even if initialization of output is performed so as to eliminate assay variations, molding variations in casing, etc. of the light-receiving elements, optical system variations can be corrected by using the ratio between an initial output value of the first light-receiving element and an initial output value of the second light-receiving element as a correction value and multiplying an output difference obtained at a time of operation by the correction value of the ratio between the initial values, and thereby a voltage difference of smoke detection can be obtained accurately.

In one embodiment, the resistor device has a positive temperature coefficient.

The temperature characteristic of the quantity of light emitted by the light-emitting device, for example, a light-emitting element, is generally negative. Thus, an output change caused by a temperature change can be reduced by using, as the above resistor (e.g. a gain resistor of an I-V conversion amplifier of an amplifier circuit), a resistor having a positive temperature characteristic.

In one embodiment, the smoke sensor further comprises a flat plate-shaped wall. The first light-receiving element, the second light-receiving element, the first switch, and the amplifier section are included in one integrated circuit. A distance from a light-emitting surface of the light-emitting device to a light-receiving surface of the first light-receiving element is same as a distance from the light-emitting surface to a light-receiving surface of the second light-receiving element. The first chamber exists on one side of the flat plate-shaped wall, while the second chamber exists on an opposite side of the flat plate-shaped wall. Furthermore, the smoke sensor also has a first interceptor preventing light from the light-emitting device from directly entering the light-receiving surface of the first light-receiving element and a second interceptor preventing light from the light-emitting device from directly entering the light-receiving surface of the second light-receiving element.

According to this embodiment, a light-emitting element, for example, can be disposed at the midpoint between an area for smoke detection and an area which does not influence smoke, and the first light-receiving element and the second light-receiving element can be arranged so as to face the wall separating the areas. In addition, the first light-receiving element and the second light-receiving element can be arranged in positions where wirings connected between the light-receiving elements and an integrated circuit (IC) which is an amplifier circuit are short and have the same length.

Thus, the quantity of noise coming on the wirings connected between the light-receiving elements and the amplifier circuit can be about the same and thereby a change in an output difference can be reduced. Furthermore, by integrating the first light-receiving element, the second light-receiving element, the switch, and the amplifier circuit, the lengths of wirings connected between the light-receiving elements and the amplifier circuit can be reduced and the difference between the characteristics of the first and second light-receiving elements can be reduced, so that a change in an output difference can be further reduced.

Electronic equipment according to an aspect of the present invention comprises the smoke sensor according to the present invention.

According to this invention, in the smoke sensor, an output can be easily corrected and various varying factors can be corrected accurately. Furthermore, the cost of manufacturing can be reduced.

BRIEF DESCRIPTION OF THE DRAWINGS

The present invention will become more fully understood from the detailed description given hereinbelow and the accompanying drawings which are given by way of illustration only, and thus are not intended to limit the present invention, and wherein.

DETAILED DESCRIPTION OF THE INVENTION

The present invention will be described in detail below with reference to embodiments shown in the figures.

Figure 1:
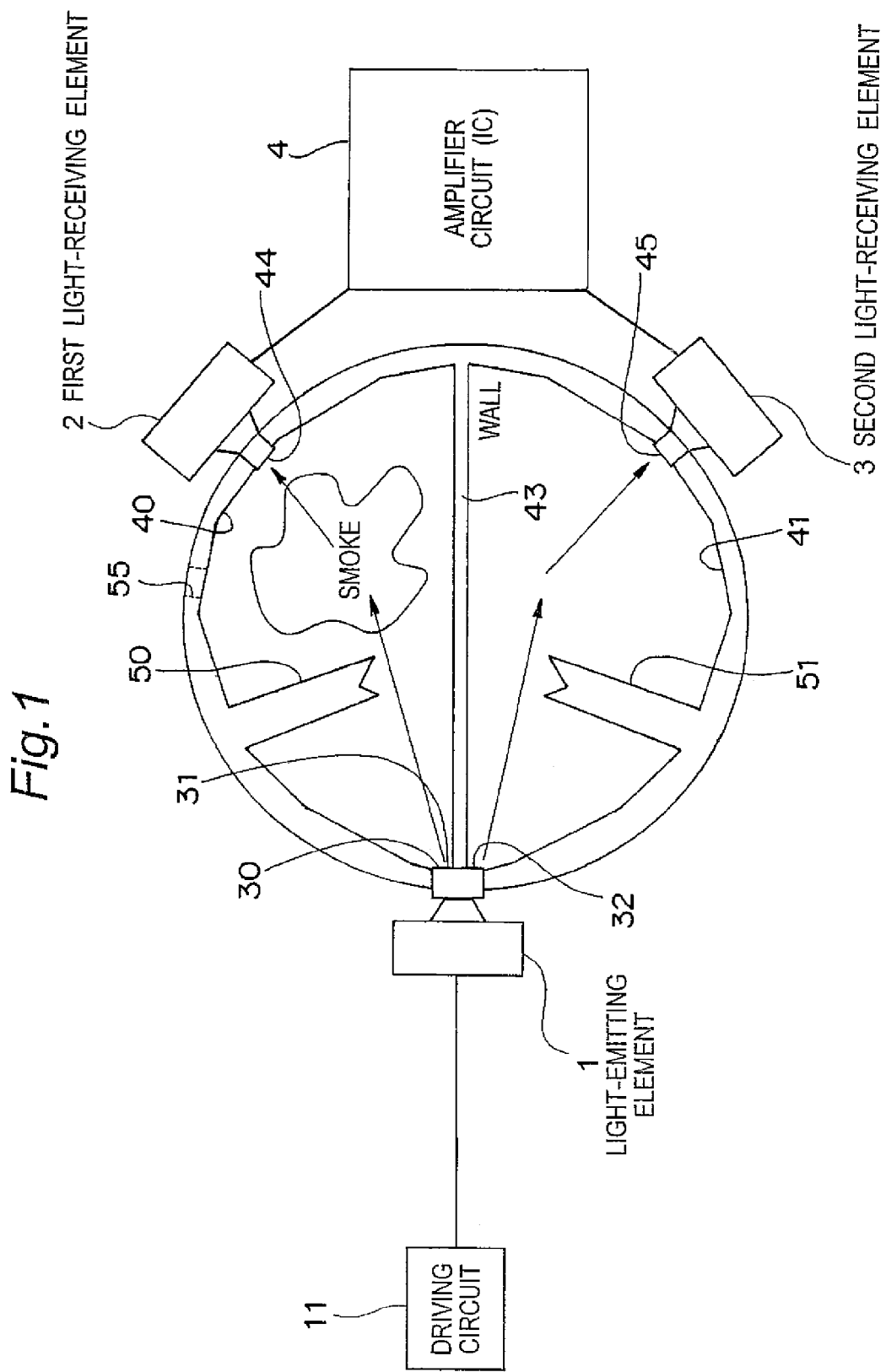
FIG. 1 is a schematic diagram of a smoke sensor of a first embodiment of the present invention.

FIG. 1 is a schematic diagram of a smoke sensor of a first embodiment of the present invention. In FIG. 1, in a smoke detection region, a cross section of the smoke sensor is shown which is taken along a plane including a normal of the light-receiving surface of a first light-receiving element 2, a normal of a surface of a wall 43, and the center of the light-receiving surface of the first light-receiving element 2.

The smoke sensor has a light-emitting element (LED in this embodiment) as a light-emitting device, the first light-receiving element 2, a second light-receiving element 3, an amplifier circuit (IC) 4 as an amplifier section, and a driving circuit 11. In this embodiment, each of the first light-receiving element 2 and the second light-receiving element 3 is a photodiode.

The light-emitting element 1 emits light when electric power is supplied from the driving circuit 11. The first light-receiving element 2 receives light which has been emitted from the light-emitting element 1 and has been reflected by smoke or has passed through smoke, while the second light-receiving element 3 receives light which has been emitted from the light-emitting element 1 and has passed through only a region where there is no smoke. The smoke sensor has an internal partition wall (simply referred to as a wall hereinafter) 13 substantially shaped like a flat plate, a first chamber 40 which is located on one side of the wall and into which smoke can flow, and a second chamber 41 which is located on the other side of the wall and into which smoke cannot flow. Light which has been emitted from the light-emitting element 1 and has traveled in the first chamber 40 is received by the first light-receiving element 2, while light which has been emitted from the light-emitting element 1 and has traveled in the second chamber 41 is received by the second light-receiving element 3.

One of end faces opposed in the longitudinal direction of the wall is in contact with the light-emitting surface 30 of the light-emitting element 1. The light-emitting surface 30 of the light-emitting element 1 is divided into two portions by the wall 43. These two light-emitting surface portions 31 and 32 (referred to as a first light-emitting surface portion 31 and a second light-emitting surface portion 32 hereinafter) are located plane-symmetrically with respect to the wall 43.

The first chamber 40 and the second chamber 41 are substantially symmetrical in shape with the wall 43 in between (different points in shape will be described later). One of end faces opposed in the direction of thickness of the wall 43 constitutes part of the inner periphery of the first chamber 40, while the other of the end faces in the direction of thickness of the wall 43 constitutes part of the inner periphery of the second chamber 41. The first light-emitting surface portion 31 constitutes another part of the inner periphery of the first chamber 40, while the second light-emitting surface portion 32 constitutes another part of the inner periphery of the second chamber 41. Light emitted from the first light-emitting surface portion 31 and light emitted from the second light-emitting surface portion 32 are plane-symmetrical with respect to the wall 43. A light-receiving surface 44 of the first light-receiving element 2 constitutes part of the inner periphery of the first chamber 40, while a light-receiving surface 45 of the second light-receiving element 3 constitutes part of the inner periphery of the second chamber 41. The light-receiving surface 44 of the first light-receiving element 2 and the light-receiving surface 45 of the second light-receiving element 3 are located plane-symmetrically with respect to the wall 43.

The smoke sensor has a first partition 50 as a first interceptor and a second partition 51 as a second interceptor. The first partition 50 protrudes from the inner periphery of the first chamber 40 to the inside of the first chamber 40, while the second partition 51 protrudes from the inner periphery of the second chamber 41 to the inside of the second chamber 41. The first partition 50 and the second partition 51 are located plane-symmetrically with respect to the wall 43.

The first partition 50 intercepts part (light causing only a noise) of light from the first light-emitting surface portion 31 to increase the S/N (signal-to-noise) ratio of an output signal of the first light-receiving element 2, while the second partition 51 intercepts part (light causing only a noise) of light from the second light-emitting surface portion 32 to increase the S/N (signal-to-noise) ratio of an output signal of the second light-receiving element 3. The distance (shortest distance) between the wall 43 and the first partition 50 is shorter than the distance (shortest distance) between the wall 43 and the light-receiving surface 44 of the first light-receiving element 2. The first partition 50 does not allow light from the first light-emitting surface portion 31 to directly enter the first light-receiving element 2, while the second partition 51 does not allow light from the second light-emitting surface portion 32 to directly enter the second light-receiving element 3.

The smoke sensor has a smoke passage 55 providing communication between the inside of the first chamber 40 and a space outside the smoke sensor, and the first chamber 40 communicates with the outside. On the other hand, the second chamber 41 is completely sealed from the outside. The smoke density of the second chamber 41 is set to zero as an example of a predetermined value. Another value can be adopted as the predetermined value of the smoke density of the second chamber 41.

The first chamber 40 is different from the second chamber 41 only in having an opening which communicates with the smoke passage 55. A connecting wire connected between the first light-receiving element 2 and the amplifier circuit 4 is the same as a connecting wire connected between the second light-receiving element 3 and the amplifier circuit 4, and the length of the connecting wire connected between the first light-receiving element 2 and the amplifier circuit 4 is the same as that of the connecting wire connected between the second light-receiving element 3 and the amplifier circuit 4. In this way, a phenomenon such as increasing a difference in noise between a signal from the first light-receiving element 2 and a signal from the second light-receiving element 3 is suppressed.

Figure 2:
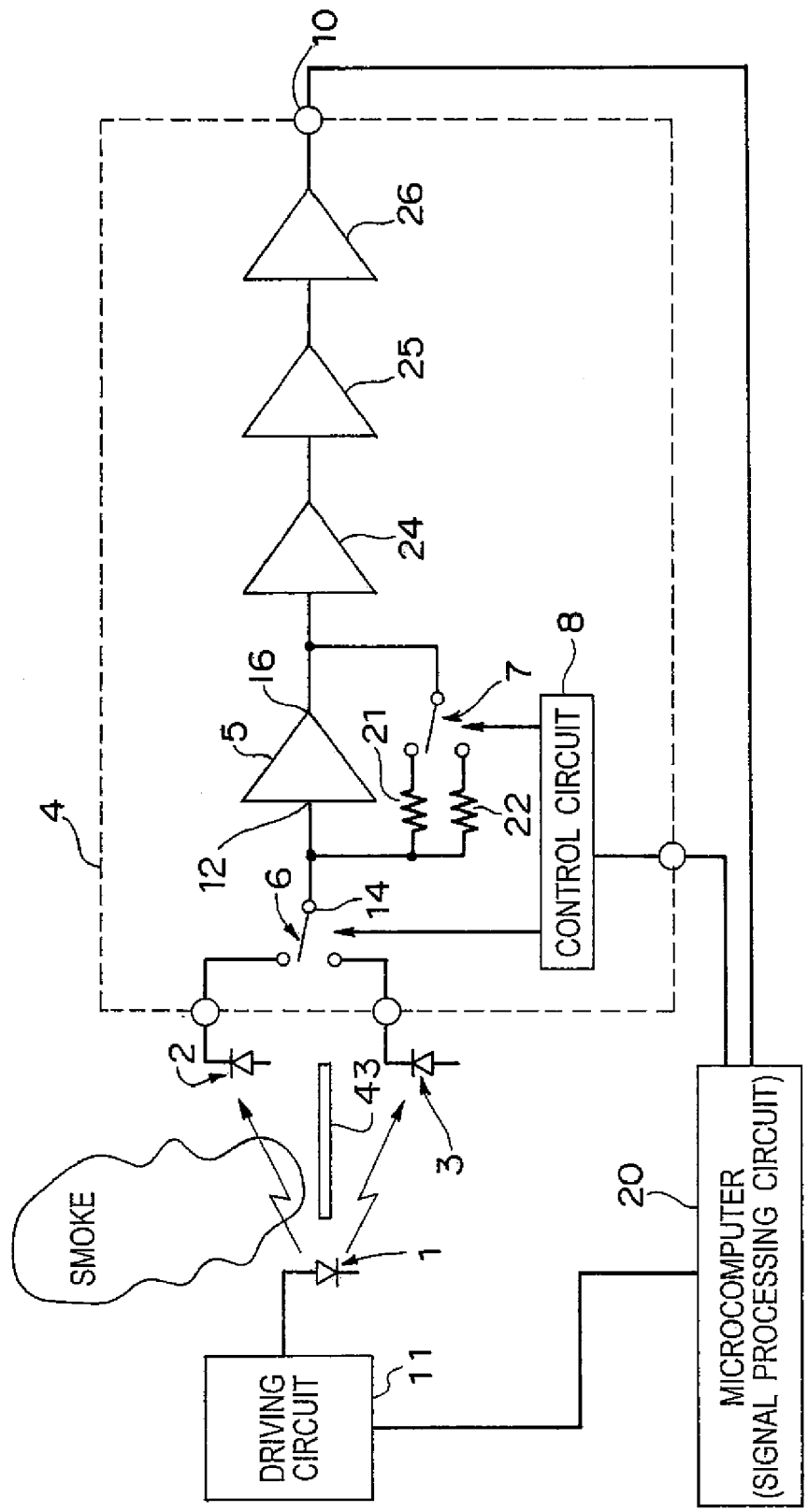
FIG. 2 is a schematic diagram showing the configuration of an amplifier circuit included in the smoke sensor of the first embodiment.

FIG. 2 is a schematic diagram showing the configuration of the amplifier circuit 4.

The amplifier circuit 4 has a first changeover switch 6 as a first switch. Portions following the first changeover switch 6 in the amplifier circuit 4 (portions other than the first changeover switch 6 in the amplifier circuit 4) constitute an amplifier section.

Outputs of the first light-receiving element 2 and the second light-receiving element 3 are selectively inputted to the amplifier circuit 4 through the first changeover switch 6, and are amplified and controlled by the amplifier circuit 4.

The amplifier circuit 4 has a first amplifier 5 which is an I-V amplifier (current-voltage conversion amplifier) as a current-voltage conversion section converting a current signal inputted to the amplifier circuit 4 to a voltage signal. The first amplifier 5 has a feedback circuit, and the resistance value of the feedback resistance can be changed by a second changeover switch 7 as a second switch to change the amplification factor.

Specifically, an output terminal 14 of the first changeover switch 6 is electrically connected with an input terminal 12 of the I-V amplifier 5. Furthermore, one terminal of each of a first feedback resistor 21 and a second feedback resistor 22 is connected with the output terminal 14 of the first changeover switch 6 and the input terminal 12 of the I-V amplifier 5, and the other terminal of any one of the first feedback resistor 21 and the second feedback resistor 22 is selectively connected to an output terminal 16 of the I-V amplifier 5 by the second changeover switch 7. The feedback may be either positive feedback or negative feedback. The amplification factor of the first amplifier 5 can be increased in the case of positive feedback, and can be made accurate in the case of negative feedback.

Like this, the gain of the I-V amplifier 5 is allowed to be changed by the second changeover switch 7. A second amplifier 24, a third amplifier 25, and a fourth amplifier are connected in series with the output terminal 16 of the I-V amplifier 5.

An output terminal of the fourth amplifier 26 corresponds to an output terminal 10 of the amplifier circuit 4. The output terminal 10 of the amplifier circuit 4 is connected with a microcomputer 20 as a signal processing circuit. A voltage after amplification of each of the light-receiving elements 2 and 3 is supplied to and processed by the microcomputer 20.

Furthermore, the microcomputer 20 controls the driving circuit 11. The microcomputer 20 outputs a command signal to a control circuit 8. The control circuit 8 controls the first changeover switch 6 and the second changeover switch 7 on the basis of a command signal from the microcomputer 20.

The amplifier circuit 4 is intermittently driven by the external microcomputer 20 to reduce the current consumption. When the amplifier circuit 4 comes into a state of operational stability during an operation of the amplifier circuit 4, electric power is supplied from the driving circuit 11 controlled by the microcomputer 20 to the light-emitting element 1, which emits pulsed light.

Pulsed light emitted by the light-emitting element 1 enters the first light-receiving element 2 and the second light-receiving element 3. Then, first, the output side of the second light-receiving element 3 is connected to the input terminal 12 of the first amplifier 5 by the first changeover switch 6, and the other end of the first feedback resistor (gain resistor) 21 for the second light-receiving element is connected to the output terminal 16 of the first amplifier 5 by the second changeover switch 7. In this way, an output current of the second light-receiving element 3 is converted to a voltage and amplified, and an output voltage obtained by processing by the following amplifiers 24, 25, and 26 is outputted to the microcomputer 20 through the output terminal 10.

After that, the output side of the first light-receiving element 2 is connected to the input terminal 12 of the first amplifier 5 by the first changeover switch 6, and the other end of the second feedback resistor (gain resistor) 22 for the first light-receiving element is connected to the output terminal 16 of the first amplifier 5 by the second changeover switch 7. In this way, an output current of the first light-receiving element 2 is converted to a voltage and amplified, and an output voltage obtained by processing of the second, third, and fourth amplifiers 24, 25, and 26 following the first amplifier 5 is outputted to the microcomputer 20 through the output terminal 10.

Figure 3:
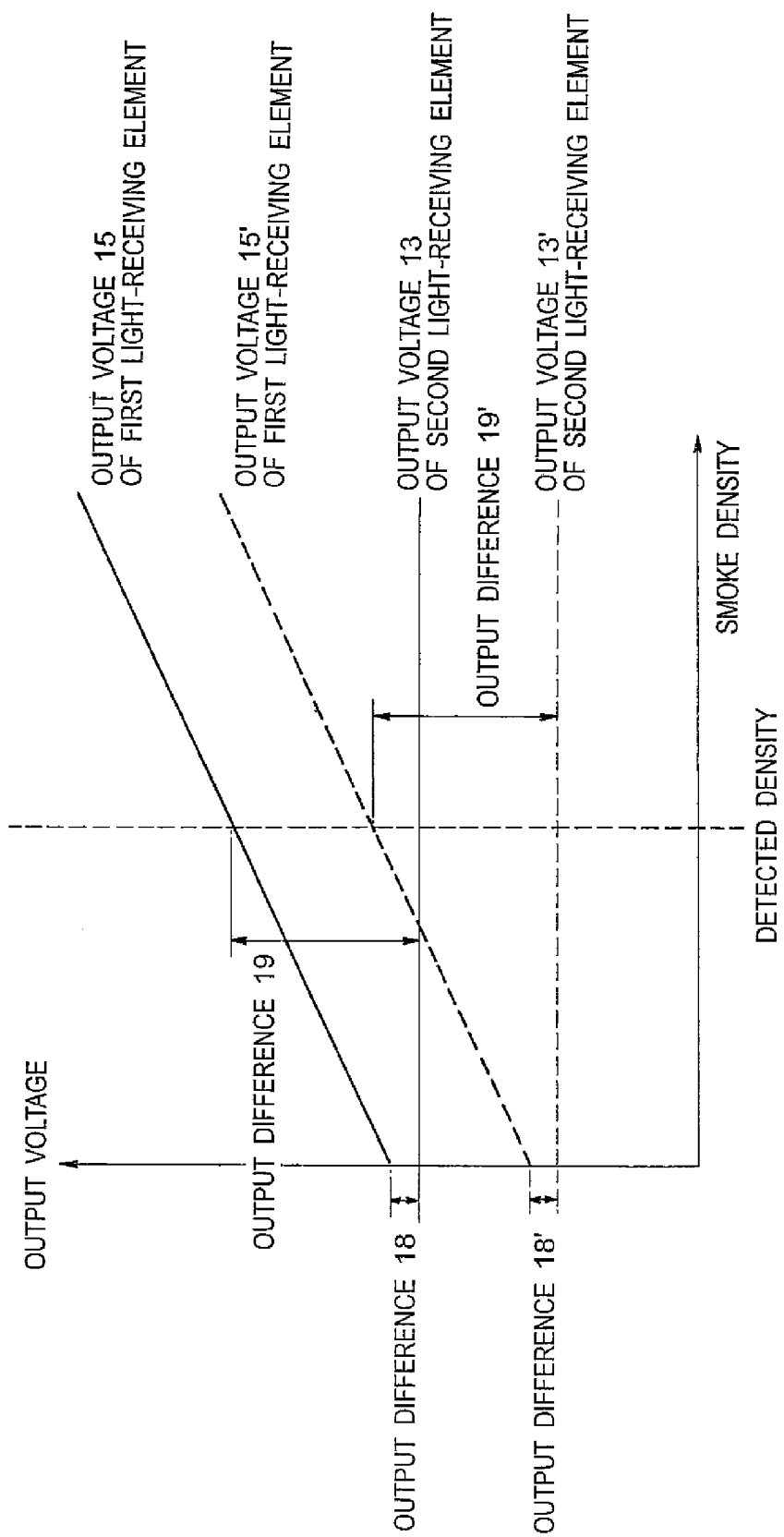
FIG. 3 is a schematic diagram showing the relation between the density of smoke and output voltages of first and second light-receiving elements in the smoke sensor of the first embodiment.

FIG. 3 is a schematic diagram showing the relation between the density of smoke and output voltages of the light-receiving elements 2 and 3 in the smoke sensor of the first embodiment.

As described above, in the smoke sensor of the first embodiment, because the feedback resistance value is changed between the feedback resistor 21 and the feedback resistor 22 in an operation of obtaining an output 13 by amplifying an output of the second light-receiving element 3 with the amplifier section and in an operation of obtaining an output 15 by amplifying an output of the first light-receiving element 2 with the amplifier section, the amplification factor is changed between the first light-receiving element 2 and the second light-receiving element 3.

Thus, the smoke sensor can be set in advance such that the difference between an output obtained by amplifying an output of the first light-receiving element 2 with the amplifier section and an output obtained by amplifying an output of the second light-receiving element 3 with the amplifier section in a state that there is no smoke (this is referred to as a normal state) assumes a given value or less. This output difference 18 of the given value or less in a state that there is no smoke is taken as a normal output difference voltage. The given value may be arbitrarily set according to the power supply voltage applied. For example, when the power supply voltage applied to the smoke sensor is 3.0 V, the given value may be set to 1.6 V or less.

When smoke flows into the smoke sensor, the output current of the first light-emitting element 12 increases and the value of an output 15 obtained by amplification of the output current increases, while the output 13 of the second light-receiving element 3 located in a position where there is no influence of smoke does not change, so that the output difference 19 in voltage between the output 15 and the output 13 is larger than the normal output difference 18. Then, the microcomputer 20 performs predetermined computation based on the normal output difference voltage to detect a smoke density from the output difference 19. The microcomputer 20 constitutes a density detecting section.

In the first embodiment, the first light-receiving element 2 and the second light-receiving element 3 receive light from the same light-emitting element 1. Thus, when the quantity of light emitted by the light-emitting element changes due to its temperature characteristic, deterioration, or the like, the received light output currents of the first light-receiving element 2 and the second light-receiving element 3 similarly change, and therefore an output voltage 13 which is a signal from the first light-receiving element 2 amplified by the amplifier circuit 4 and an output voltage 15 which is a signal from the second light-receiving element 3 amplified by the amplifier circuit 4 similarly change to output voltages 13' and 15', respectively.

Thus, there is little difference between the output difference 18' at the smoke density of zero after the change of the quantity of light emitted by the light-emitting element 1 and the output difference 18 at the smoke density of zero before the change of the quantity of light emitted by the light-emitting element 1, so that there is little difference between the output difference 19' at a smoke detection density to be judged as smoke detection after the change of the quantity of light emitted by the light-emitting element 1 and the output difference 19 at the smoke detection density to be judged as smoke detection before the change of the quantity of light emitted by the light-emitting element 1. Therefore correction is hardly required before and after the change of the quantity of light emitted by the light-emitting element 1.

Even if an output voltage which is a signal from the first light-receiving element 2 amplified by the amplifier circuit 4 and an output voltage which is a signal from the second light-receiving element 3 amplified by the amplifier circuit 4 change due to the temperature dependence of the amplifying circuit 4, the received light output currents of the first light-receiving element 2 and the second light-receiving element 3 are amplified by the same amplifier circuit 4, thereby causing little difference in change of the amplification factor, so that there is little difference between an output difference at the smoke density of zero and an output difference at a smoke detection density to be judged as smoke detection.

Both of the received light output currents of the first light-receiving element 2 and the second light-receiving element 3 are processed in the same process in the integrated circuit (IC), so that there is little difference between two signals.

In this connection, even if initialization of the output is performed so as to eliminate assay variations, molding variations in casing, etc. of the two light-receiving elements 2 and 3, variations based on individual differences may be generated. More specifically, if variations in the output voltage 13 of the second light-receiving element 3 are larger than a predetermined value when the amplification factor of the amplifier circuit is adjusted based on the output voltage 15 of the first light-receiving element 2, when there is a large temperature change, the difference between the output difference 19' after the temperature change and the output difference 19 before the temperature change is large. Furthermore, the output difference 19 and the output difference 19' vary based on individual differences of the sensor.

In this case, the ratio between an output value 15 of the first light-receiving element 2 and an output value 13 of the second light-receiving element 3 in the case that there is no smoke is stored in the microcomputer 20 as a correction value A of an initial value for the case that there is no smoke. Then, a difference between an output 13 of the second light-receiving element multiplied by the correction value A and an output 15 of the first-light receiving element is obtained as a detection signal. Specifically, the detection signal is given by the following equation:

Detection signal=(Output signal 15 of first light-receiving element 2)–$A$×(Output signal 13 of second light-receiving element 3), where A=(Initial value of output value 15 of first light-receiving element 2)/(Initial value of output value 13 of second light-receiving element 3).

Likewise, the ratio between an output value 15' of the first light-receiving element 2 and an output value 13' of the second light-receiving element 3 in the case that there is no smoke resulting from variations of the optical system is stored in the microcomputer 20 as a correction value B. Then, a difference between an output 13' of the second light-receiving element multiplied by the correction value B and an output 15' of the first light-receiving element is obtained as a detection signal. In other words, the detection signal after variations of the optical system is given by the following equation.

Detection signal=(Output signal 15' of first light-receiving element 2)–$B$×(Output signal 13' of second light-receiving element 3), where B=(Initial value of output value 15' of first light-receiving element 2)/(Initial value of output value 13' of second light-receiving element 3).

As described above, the correction values A and B are set, and variations in output due to variations of the optical system in the case that there is no smoke are corrected in advance by the above equations.

In this connection, it is needless to say that the number of amplifiers following the current-voltage conversion amplifier is not limited to three like the first embodiment and may be one or four or more.

Furthermore, the first chamber into which smoke can flow may have a smoke intake passage and a smoke discharge passage, and smoke may be circulated by a fan or the like. In this case, it is needless to say that when the flow of smoke is let to pass through a position facing the light-receiving surface of the first light-receiving element in the normal direction of the light-receiving surface, the density of the smoke can be detected accurately.

Figure 4:
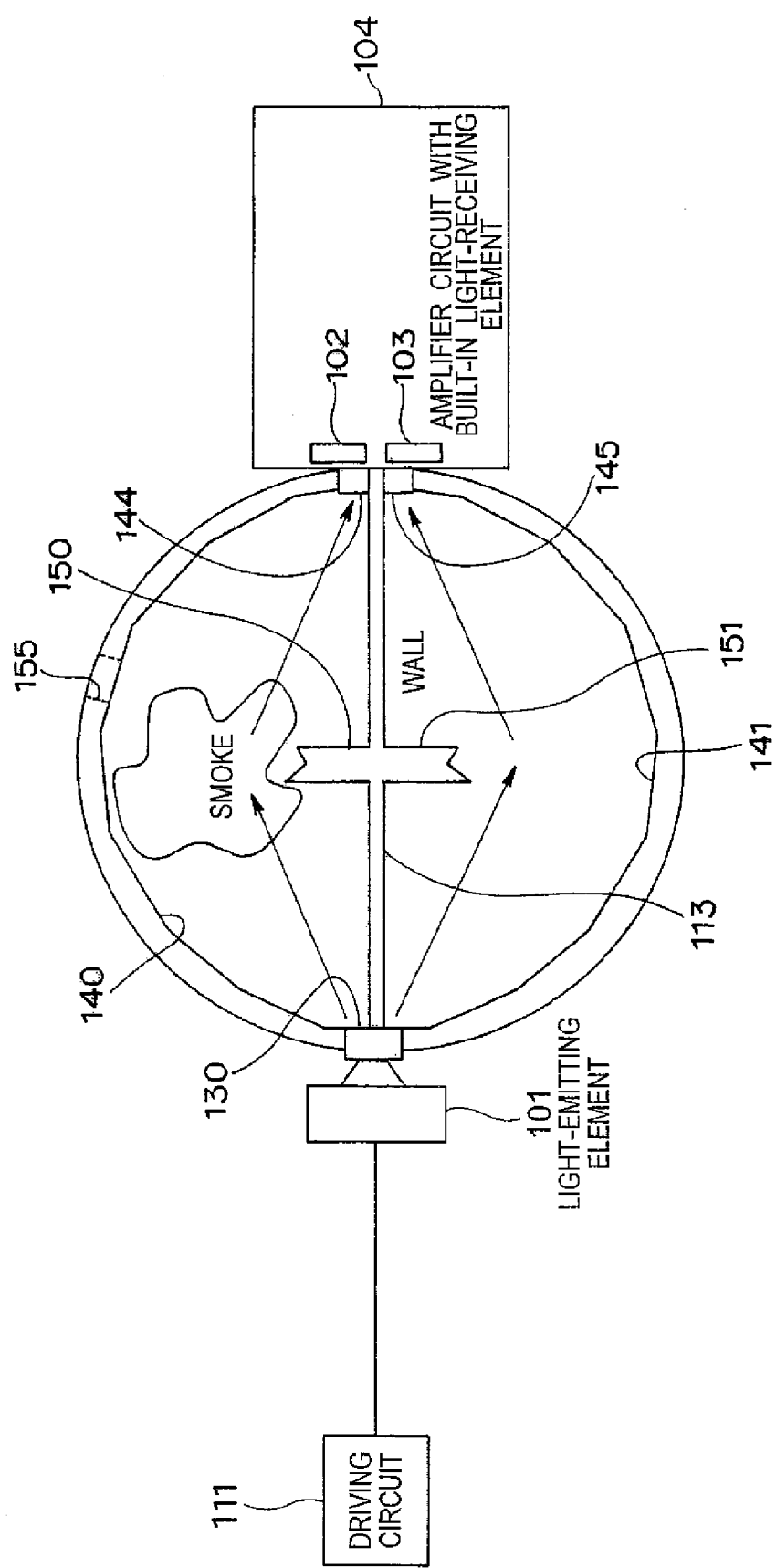
FIG. 4 is a schematic diagram showing a smoke sensor of a second embodiment.

FIG. 4 is a schematic diagram showing a smoke sensor of a second embodiment. In FIG. 4, in a smoke detection region, a cross section of the smoke sensor is shown which is taken along a plane including the normal of the light-receiving surface of a first light-receiving element 102, the normal of a surface of a wall 113, and the center of the light-receiving surface of the first light-receiving element 102.

The second embodiment is the same as the first embodiment in that a first chamber 140 and a second chamber 141 are plane-symmetrical in shape with respect to the wall, except for an opening of a smoke passage 155 of the first chamber 140, that the light-emitting surface of a light-emitting element 101, the light-receiving surface 144 of a first light-receiving element 102, and the light-receiving surface 145 of a second light-receiving element 103 constitute part of the inner peripheries of the chambers, and that the light-receiving surface 144 of the first light-receiving element 102 and the light-receiving surface 145 of the second light-receiving element 103 are plane-symmetrical with respect to the wall.

In the second embodiment, description about the same configuration, operation, and effect as those of the first embodiment is omitted.

In the second embodiment, the first light-receiving element 102 and the second light-receiving element 103 are included and integrated with an amplifier circuit 104.

In the smoke sensor of the second embodiment, a first partition 150 as a first interceptor protrudes from the wall 113 to the inside of the first chamber 140, and a second partition 151 as a second interceptor protrudes from the wall 113 to the inside of the second chamber 141. Furthermore, the first light-receiving element 102 is disposed so as to face the light-emitting element 101 in the longitudinal direction of the wall 113 on one side of the wall 113 at an end opposite to the light-emitting element 101 in the longitudinal direction of the wall 113, and the second light-receiving element 103 is disposed so as to face the light-emitting element 101 in the longitudinal direction of the wall 113 on the other side of the wall 113 at an end opposite to the light-emitting element 101 in the longitudinal direction of the wall 113.

To be precise, the normal direction of the light-emitting surface 130 of the light-emitting element 101 is substantially parallel with the normal directions of the light-receiving surfaces 144 and 145 of the first light-receiving element 102 and the second light-receiving element 103. In other words, the light-emitting surface 130 faces the light-receiving surface 144 of the first light-receiving element 102 and the light-receiving surface 145 of the second light-receiving element 103 with a space in between in the longitudinal direction of the wall.

The first partition 150 prevents light emitted from the light-emitting element 101 from directly entering the light-receiving surface 144 of the first light-receiving element 102, and the second partition 151 prevents light emitted from the light-emitting element 101 from directly entering the light-receiving surface 145 of the second light-receiving element 103.

The first partition 150 intercepts light emitted from the light-emitting surface 130 of the light-emitting element 101 in the longitudinal direction of the wall 113 so as to prevent the light from directly reaching the light-receiving surface 144 of the first light-receiving element 102. Furthermore, the second partition 151 intercepts light emitted from the light-emitting surface 130 of the light-emitting element 101 in the longitudinal direction of the wall 113 so as to prevent the light from directly reaching the light-receiving surface 145 of the second light-receiving element 103.

Figure 5:
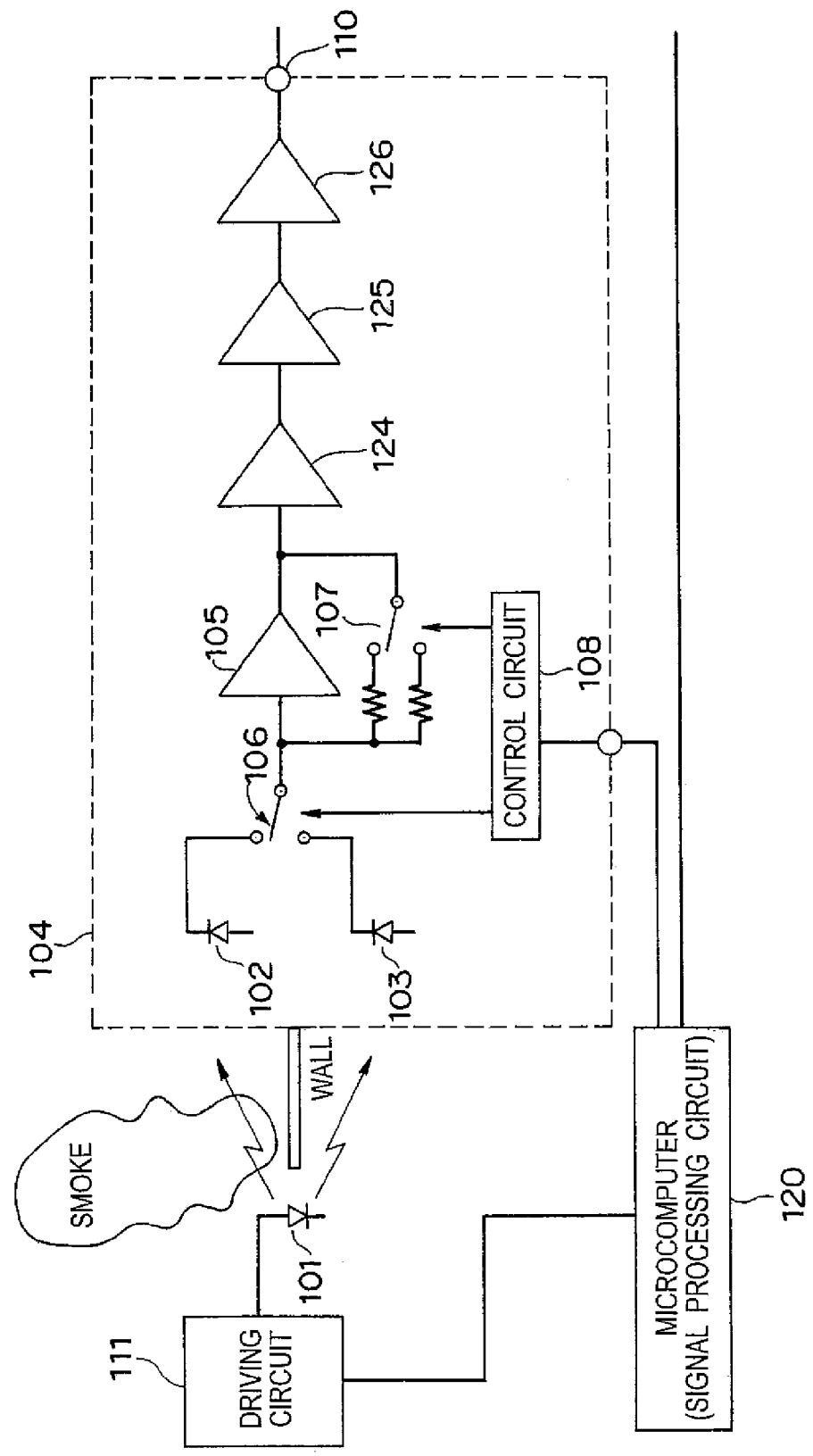
FIG. 5 is a schematic diagram showing the configuration of an amplifier circuit included in the smoke sensor of the second embodiment.

FIG. 5 schematically shows the configuration of the amplifier circuit 104 of the smoke sensor of the second embodiment.

In FIG. 5, the reference numeral 105 denotes a current-voltage conversion amplifier, 106 denotes a first changeover switch, 107 denotes a second changeover switch, 108 denotes a control circuit, 110 denotes an output terminal of the amplifier circuit 104, 111 denotes a driving circuit, 120 denotes a microcomputer as a density detecting section, and 124, 125, and 126 denote amplifiers.

As shown in FIG. 5, in the second embodiment, the first light-receiving element 102 and the second light-receiving element 103 are integrated into the amplifier circuit 104 (integrated circuit) to be part of the amplifier circuit 104.

According to the second embodiment, the first and second light-receiving elements 102 and 103 are built in the amplifier circuit 104, so that variations in output between the first light-receiving element 102 and the second light-receiving element 103 can be prevented. Furthermore, the first light-receiving element 102 and the second-light receiving element 103 are connected with the amplifier section in the amplifier circuit 104, so that signal noise can be significantly reduced.

When a smoke sensor according to this invention is mounted on electronic equipment such as an air cleaner or a fire alarm, even if the light-emitting element deteriorates as time goes by or the temperature significantly changes in the electronic equipment, the density of smoke can be detected accurately. Thus, for example, the degree of air cleaning can be judged accurately in the air cleaner, or fire can be judged accurately in the fire alarm.

The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A smoke sensor comprising:
a light-emitting device emitting light;
a first chamber;
a smoke passage providing communication between inside of the first chamber and outside of the first chamber;
a second chamber having a density of smoke of a predetermined value;
a first light-receiving element receiving light which has traveled in the first chamber after being emitted from the light-emitting device directly to the first chamber or light which has traveled in the first chamber after being emitted from the light-emitting device and entering the first chamber through only a place having a density of smoke of zero;
a second light-receiving element receiving light which has traveled in the second chamber after being emitted from the light-emitting device directly to the second chamber or light which has traveled in the second chamber after being emitted from the light-emitting device and entering the second chamber through only a place having a density of smoke of zero;
a first switch receiving and selectively outputting a signal from the first light-receiving element and a signal from the second light-receiving element;
an amplifier section amplifying a signal from the first switch; and
a density detecting section detecting a density of smoke in the first chamber on the basis of a first amplified signal which is a signal from the first light-receiving element amplified by the amplifier section and a second amplified signal which is a signal from the second light-receiving element amplified by the amplifier section.

2. The smoke sensor as claimed in claim 1, wherein:
each of the first amplified signal and the second amplified signal is a voltage signal;
a light-receiving surface of the first light-receiving element is disposed in the first chamber and a light-receiving surface of the second light-receiving element is disposed in the second chamber;
a distance from a light-emitting surface of the light-emitting device to the light-receiving surface of the first light-receiving element is same as a distance from the light-emitting surface to the light-receiving surface of the second light-receiving element;
the predetermined value of the density of smoke in the second chamber is zero; and
the first amplified signal has a magnitude same as a magnitude of the second amplified signal in a state that the density of smoke in the first chamber is zero.

3. The smoke sensor as claimed in claim 1, wherein the amplifier section has one or more amplifiers.

4. The smoke sensor as claimed in claim 1, wherein:
the amplifier section has a current-voltage conversion section;
the current-voltage conversion section has an input terminal connected with an output terminal of the first switch, an output terminal, and a resistor device connected between the input terminal and the output terminal of the current-voltage conversion section; and
the resistor device provides resistances which are different between a case that a signal from the first light-receiving element is processed by the current-voltage conversion section and a case that a signal from the second light-receiving element is processed by the current-voltage conversion section.

5. The smoke sensor as claimed in claim 4, wherein:
the resistor device includes a first resistor one end of which is connected with the input terminal of the current-voltage conversion section, and a second resistor one end of which is connected with the input terminal of the current-voltage conversion section;
the current-voltage conversion section further has a second switch an output terminal of which is connected with the output terminal of the current-voltage conversion section; and
the smoke sensor further comprises a control circuit which outputs a control signal for connecting an input terminal of the second switch to another end of the first resistor when a signal from the first light-receiving element is processed by the current-voltage conversion section, while outputting a control signal for connecting the input terminal of the second switch to another end of the second resistor when a signal from the second light-receiving element is processed by the current-voltage conversion section.

6. The smoke sensor as claimed in claim 4, wherein the resistor device has a positive temperature coefficient.

7. The smoke sensor as claimed in claim 1, further comprising a flat plate-shaped wall, wherein:
- the first light-receiving element, the second light-receiving element, the first switch, and the amplifier section are included in one integrated circuit;
- a distance from a light-emitting surface of the light-emitting device to a light-receiving surface of the first light-receiving element is same as a distance from the light-emitting surface to a light-receiving surface of the second light-receiving element;
- the first chamber exists on one side of the flat plate-shaped wall, while the second chamber exists on an opposite side of the flat plate-shaped wall; and
- the smoke sensor further comprises a first interceptor preventing light from the light-emitting device from directly entering the light-receiving surface of the first light-receiving element and a second interceptor preventing light from the light-emitting device from directly entering the light-receiving surface of the second light-receiving element.

8. Electronic equipment comprising the smoke sensor as claimed in claim 1.

* * * * *